(12) United States Patent
Tomatsu

(10) Patent No.: US 11,921,280 B2
(45) Date of Patent: Mar. 5, 2024

(54) PHOTOELECTRIC COMPOSITE MODULE, CAMERA HEAD, AND ENDOSCOPIC DEVICE

(71) Applicant: Sony Olympus Medical Solutions Inc., Tokyo (JP)

(72) Inventor: Kei Tomatsu, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 146 days.

(21) Appl. No.: 17/313,033

(22) Filed: May 6, 2021

(65) Prior Publication Data

US 2021/0255452 A1 Aug. 19, 2021

Related U.S. Application Data

(63) Continuation of application No. 14/815,383, filed on Jul. 31, 2015, now Pat. No. 11,036,041, which is a
(Continued)

(30) Foreign Application Priority Data

Jan. 16, 2014 (JP) ................................. 2014-006258

(51) Int. Cl.
*A61B 1/00* (2006.01)
*A61B 1/04* (2006.01)
(Continued)

(52) U.S. Cl.
CPC ...... *G02B 23/2484* (2013.01); *A61B 1/00013* (2013.01); *A61B 1/00018* (2013.01);
(Continued)

(58) Field of Classification Search
CPC ....... A61B 1/00163; A61B 1/04; A61B 1/042; A61B 1/05; A61B 1/045; A61B 1/00174;
(Continued)

(56) References Cited

U.S. PATENT DOCUMENTS 4,677,471 A 6/1987 Takamura et al.
4,745,470 A 5/1988 Yabe et al.
(Continued)

FOREIGN PATENT DOCUMENTS

EP 1 752 082 A1 2/2007
JP 2001-258835 A 9/2001
(Continued)

OTHER PUBLICATIONS

Office Action dated Sep. 25, 2018 in corresponding Japanese Patent Application No. 2017234676, 4 pages.
(Continued)

*Primary Examiner* — Ryan N Henderson
*Assistant Examiner* — Pamela F Wu
(74) *Attorney, Agent, or Firm* — XSENSUS LLP

(57) ABSTRACT

There is provided a photoelectric composite module according to the present disclosure including: a first connecting member having an outer frame having a tubular shape, and a plurality of contacts provided in an interior of the outer frame; a first printed board on which a photoelectric conversion element configured to convert an electrical signal into an optical signal is mounted, and which is configured to act as a relay between the contacts and the photoelectric conversion element; and a second printed board configured to act as a relay between the contacts and an electrical signal cable. The first printed board and the second printed board are three-dimensionally arranged.

19 Claims, 13 Drawing Sheets

Related U.S. Application Data continuation of application No. PCT/JP2014/084326, filed on Dec. 25, 2014.

(51) Int. Cl.
| | | |
|---|---|---|
| *A61B 1/045* | (2006.01) | |
| *G02B 23/24* | (2006.01) | |
| *H04N 23/51* | (2023.01) | |
| *H04N 23/54* | (2023.01) | |
| *H04N 23/56* | (2023.01) | |
| *H04N 23/57* | (2023.01) | |
| *H01R 9/05* | (2006.01) | |
| *H04N 23/50* | (2023.01) | |

(52) U.S. Cl.
CPC ...... *A61B 1/00045* (2013.01); *A61B 1/00124* (2013.01); *A61B 1/042* (2013.01); *A61B 1/045* (2013.01); *G02B 23/2476* (2013.01); *H04N 23/51* (2023.01); *H04N 23/54* (2023.01); *H04N 23/56* (2023.01); *H04N 23/57* (2023.01); *A61B 1/00105* (2013.01); *H01R 9/0515* (2013.01); *H04N 23/555* (2023.01)

(58) Field of Classification Search
CPC ............ A61B 1/00177; A61B 1/00181; A61B 1/00183; A61B 1/00193–00195; H04N 5/2252; H04N 5/2253; H04N 5/2257; H04N 2005/2255; H04N 1/051; H04N 23/57; H04N 23/54–555; G02B 23/2476; G02B 23/2484; G02B 23/2492; G02B 23/2407; G02B 23/2415; G02B 23/2423; G02B 23/243–2438
USPC .......................................... 600/109, 110, 160
See application file for complete search history.

(56) References Cited

U.S. PATENT DOCUMENTS

| | | | |
|---|---|---|---|
| 4,832,003 A | 5/1989 | Yabe | |
| 5,754,313 A * | 5/1998 | Pelchy | A61B 1/051 358/473 |
| 6,030,339 A | 2/2000 | Tatsuno et al. | |
| 6,080,101 A | 6/2000 | Tatsuno et al. | |
| 6,386,913 B1 | 5/2002 | Mohammad et al. | |
| 6,390,972 B1 | 5/2002 | Speier et al. | |
| 6,458,078 B1 | 10/2002 | Ludtke et al. | |
| 6,635,865 B1 * | 10/2003 | Soltyk | H04N 5/2253 250/239 |
| 6,805,665 B1 | 10/2004 | Tatsuno et al. | |
| 7,074,181 B2 | 7/2006 | Futatsugi | |
| 9,810,898 B2 | 11/2017 | Tomatsu | |
| 2002/0080233 A1 * | 6/2002 | Irion | H04N 5/2253 348/E5.025 |
| 2003/0169333 A1 | 9/2003 | Yazawa | |
| 2004/0096355 A1 | 5/2004 | Ishibiki | |
| 2004/0143162 A1 | 7/2004 | Krattiger et al. | |
| 2004/0176661 A1 | 9/2004 | Futatsugi | |
| 2004/0210208 A1 | 10/2004 | Paul et al. | |
| 2007/0038024 A1 | 2/2007 | Nakamura et al. | |
| 2007/0182842 A1 | 8/2007 | Sonnenschein et al. | |
| 2007/0219409 A1 | 9/2007 | Shimizu et al. | |
| 2007/0232860 A1 | 10/2007 | Kubo et al. | |
| 2007/0286231 A1 | 12/2007 | Kubo et al. | |
| 2008/0014803 A1 | 1/2008 | Kato et al. | |
| 2008/0249363 A1 | 10/2008 | Nakamura et al. | |
| 2009/0259101 A1 * | 10/2009 | Unsai | A61B 1/05 600/110 |
| 2009/0268019 A1 | 10/2009 | Ishii et al. | |
| 2010/0201794 A1 | 8/2010 | Kido et al. | |
| 2010/0234702 A1 | 9/2010 | Tokita | |
| 2010/0261961 A1 | 10/2010 | Scott et al. | |
| 2010/0265350 A1 * | 10/2010 | Ogasawara | H04N 5/3765 348/222.1 |
| 2011/0108716 A1 | 5/2011 | Shiraishi | |
| 2011/0211053 A1 | 9/2011 | Nakayama | |
| 2011/0245600 A1 | 10/2011 | Shii et al. | |
| 2012/0197081 A1 | 8/2012 | Kimura | |
| 2012/0206583 A1 | 8/2012 | Hoshi et al. | |
| 2012/0293641 A1 | 11/2012 | Nagamizu et al. | |
| 2012/0310043 A1 * | 12/2012 | Hu | A61B 1/051 600/109 |
| 2013/0035550 A1 | 2/2013 | Watanabe et al. | |
| 2013/0096380 A1 | 4/2013 | Matsuzawa et al. | |
| 2013/0169777 A1 * | 7/2013 | Zen | A61B 1/051 348/76 |
| 2013/0182099 A1 | 7/2013 | Nakamura et al. | |
| 2013/0258183 A1 * | 10/2013 | Kamei | H04N 5/2253 348/E5.025 |
| 2013/0303853 A1 | 11/2013 | Takahashi et al. | |
| 2014/0018613 A1 | 1/2014 | Scott et al. | |
| 2014/0018624 A1 | 1/2014 | Bayer et al. | |
| 2014/0187060 A1 | 7/2014 | Kubo | |
| 2014/0243595 A1 | 8/2014 | Endo | |
| 2014/0371530 A1 | 12/2014 | Wieters et al. | |
| 2015/0086162 A1 | 3/2015 | Miyahara et al. | |
| 2015/0293343 A1 | 10/2015 | Nagase | |
| 2015/0305606 A1 | 10/2015 | Kaneko | |
| 2015/0318924 A1 | 11/2015 | Motohara | |
| 2015/0335230 A1 | 11/2015 | Tomatsu | |
| 2015/0378144 A1 | 12/2015 | Handte et al. | |

FOREIGN PATENT DOCUMENTS

| | | |
|---|---|---|
| JP | 2004-167083 A | 6/2004 |
| JP | 2005-066129 A | 3/2005 |
| JP | 2007-244747 A | 9/2007 |
| JP | 2007-260066 A | 10/2007 |
| JP | 2010-5148 A | 1/2010 |
| JP | 2011-177263 A | 9/2011 |
| JP | 2012-79851 A | 4/2012 |
| JP | 2013-78591 A | 5/2013 |
| JP | 2015-134039 A | 7/2015 |
| WO | 2011/052408 A1 | 5/2011 |
| WO | 2012/043187 A1 | 4/2012 |
| WO | 2012/046856 A1 | 4/2012 |

OTHER PUBLICATIONS

Japanese Office Action dated Aug. 29, 2017 in Patent Application No. 2015173326.
Extended European Search Report dated Sep. 16, 2016 in Patent Application No. 14878977.9.
Extended European Search Repot dated Jun. 13, 2016 in Patent Application No. 15194598.7.
Partial European Search Report dated Mar. 11, 2016 in European Application No. 15194598.7.
Japanese Office Action dated Oct. 20, 2015 in Patent Application No. 2015166732.
Office Action dated Sep. 24, 2015 in Japanese Patent Application No. 2015166732.
Office Action dated Sep. 24, 2015 in Japanese Patent Application No. 2015166733.
International Search Report dated Mar. 24, 2015 in PCT/JP2014/084326 filed Dec. 25, 2014.
Written Opinion dated Mar. 24, 2015 in PCT/JP2014/084326 filed Dec. 25, 2014.

* cited by examiner

PHOTOELECTRIC COMPOSITE MODULE, CAMERA HEAD, AND ENDOSCOPIC DEVICE

CROSS-REFERENCE TO RELATED APPLICATIONS

This application is a continuation of U.S. application Ser. No. 14/815,383, filed Jul. 31, 2015, which is a bypass continuation of PCT filing PCT/JP2014/084326, filed Dec. 25, 2014, which claims priority to JP 2014-006258, filed Jan. 16, 2014, the entire contents of each are incorporated herein by reference.

TECHNICAL FIELD

The present disclosure relates to a photoelectric composite module, a camera head, and an endoscopic device.

BACKGROUND ART

In the past, there has been known in medical fields and industrial fields an endoscopic device using an image sensor to image the interior of an observation object such as a human being or a machine structure, and thereby to observe the interior of the observation object (see Patent Literature 1, for example).

The endoscopic device according to Patent Literature 1 is an endoscopic device with a detachable head including: an imaging device (hereinafter described also as a camera head) which includes an image sensor; a controller to control the image sensor; and a cable electrically connecting between the imaging device and the controller and configured to transmit various signals therebetween.

Accordingly, the endoscopic device according to Patent Literature 1 employs high-capacity optical transmission in consideration of the fact that image data output by the image sensor contains a large amount of information.

Specifically, the camera head includes the image sensor and a printed board electrically connected to the image sensor. On the printed board, there is mounted a photoelectric conversion element converting, into optical signals, imaging signals (electrical signals) output by the image sensor and relayed by the printed board.

Meanwhile, the cable is formed of a composite cable including electrical wires for transmitting electrical signals and an optical wire for transmitting optical signals. The electrical wires are electrically connected to the printed board, and transmit, to the printed board (image sensor), control signals and the like (electrical signals) output by the controller. The optical wire is connected to the photoelectric conversion element, and transmits, to the controller, optical signals (imaging signals) obtained through conversion by the photoelectric conversion element.

CITATION LIST

Patent Literature

Patent Literature 1: JP2011-177263A

SUMMARY OF INVENTION

Technical Problem

However, in the camera head according to Patent Literature 1, the single printed board is provided with two functions: the function of relaying, to the photoelectric conversion element, imaging signals (electrical signals) output by the image sensor; and the function of relaying, to the image sensor, control signals and the like (electrical signals) output by the controller. In addition, it is necessary to secure, on the printed board, an area for the mounting of the photoelectric conversion element.

This necessitates increasing the size of the printed board, and thus makes it difficult to achieve downsizing of the camera head, which is problematic.

The present disclosure is made in view of the above, and an objective thereof is to provide a photoelectric composite module, a camera head, and an endoscopic device which can be downsized.

Solution to Problem

In order to solve the aforementioned problem and achieve the aforementioned objective, a photoelectric composite module according to the present disclosure includes: a first connecting member having an outer frame having a tubular shape, and a plurality of contacts provided in an interior of the outer frame; a first printed board on which a photoelectric conversion element configured to convert an electrical signal into an optical signal is mounted, and which is configured to act as a relay between the contacts and the photoelectric conversion element; and a second printed board configured to act as a relay between the contacts and an electrical signal cable. The first printed board and the second printed board are three-dimensionally arranged.

With regard to the photoelectric composite module according to the present disclosure, at least part of the first printed board and at least part of the second printed board may be arranged in different plain faces.

With regard to the photoelectric composite module according to the present disclosure, at least part of the second printed board may have a curved shape. At least part of the first printed board and at least part of the second printed board may be arranged in different faces.

With regard to the photoelectric composite module according to the present disclosure, the second printed board may be formed of a flexible substrate, at least part of which is bendable.

With regard to the photoelectric composite module according to the present disclosure, the first printed board may be formed of a rigid substrate having a planar shape.

With regard to the photoelectric composite module according to the present disclosure, at least part of the first printed board and at least part of the second printed board may be arranged in an overlapping manner.

With regard to the photoelectric composite module according to the present disclosure, when the interior of the outer frame is divided into a first area and a second area other than the first area as viewed from a direction along a central axis of the outer frame, the plurality of contacts may include a plurality of first contacts provided in the first area, and a plurality of second contacts provided in the second area. The first printed board may be electrically connected to the plurality of first contacts. The second printed board may be electrically connected to the plurality of second contacts.

With regard to the photoelectric composite module according to the present disclosure, in the interior of the outer frame, the first area and the second area may be band-shaped areas being parallel to each other and each extending in a first direction orthogonal to the central axis.

With regard to the photoelectric composite module according to the present disclosure, the first area may be an area including the central axis.

With regard to the photoelectric composite module according to the present disclosure, the first area may be a band-shaped area extending in a first direction orthogonal to the central axis.

With regard to the photoelectric composite module according to the present disclosure, in the first area, the plurality of first contacts may be arranged side by side at a first pitch. In the second area, the plurality of second contacts may be arranged side by side at a second pitch, which is smaller than the first pitch.

With regard to the photoelectric composite module according to the present disclosure, the outer frame may have a cylindrical shape. The first area may be a band-shaped area including the central axis and extending in a radial direction of the outer frame.

With regard to the photoelectric composite module according to the present disclosure, the first printed board may be arranged along a central axis of the outer frame.

With regard to the photoelectric composite module according to the present disclosure, the second printed board may include a plurality of first lands electrically connected to ground wires constituting a conductor pattern provided to the second printed board, and formed in one of a central area and an other area, which excludes the central area, on a surface of the second printed board in a second direction along the surface, and a plurality of second lands electrically connected to signal wires constituting a conductor pattern provided to the second printed board, and formed in the other of the central area and the other area, which excludes the central area, on the surface of the second printed board.

With regard to the photoelectric composite module according to the present disclosure, the one may be the central area on the surface of the second printed board.

With regard to the photoelectric composite module according to the present disclosure, a plurality of the electrical signal cables each formed of a coaxial cable may be provided. Each of the plurality of electrical signal cables may be electrically connected to a corresponding pair of the first land and the second land which is adjacent to the first land. The first land and the second land of each of the pairs are formed to be lined up in an inclined direction with respect to the second direction on the surface of the second printed board.

With regard to the photoelectric composite module according to the present disclosure, the first printed board may be electrically connected to a plurality of first contacts arranged side by side in two rows in the interior of the outer frame, the plurality of first contacts being included in the plurality of contacts. The plurality of first contacts may include respective first pin-shaped portions being elastically deformable and protruding toward a side where the first printed board and the second printed board are arranged. When the first printed board is inserted between a first row of the two rows of the first contacts and a second row of the two rows of the first contacts, a plurality of the first pin-shaped portions hold the first printed board while being elastically deformed, and are electrically connected to the first printed board.

With regard to the photoelectric composite module according to the present disclosure, at least one of the plurality of contacts may include a pin-shaped portion protruding toward a side where the first printed board and the second printed board are arranged. The second printed board may be formed of a flexible substrate having a first connecting part having a hole through which the pin-shaped portion is inserted, the first connecting part being electrically connected to the at least one of the plurality of contacts, and a second connecting part arranged at a position overlapping with the first printed board when bent with respect to the first connecting part, the second connecting part being electrically connected to the electrical signal cable.

A camera head according to the present disclosure is a camera head used in an endoscopic device, and includes: the photoelectric composite module; and an image sensor electrically connected to the first printed board and the second printed board through the first connecting member.

With regard to the camera head according to the present disclosure, the camera head may further include: a second connecting member mechanically and electrically connected to the first connecting member; and a casing to which the second connecting member is attached. The image sensor is housed in the casing and electrically connected to the first printed board and the second printed board through the first connecting member and the second connecting member.

An endoscopic device according to the present disclosure may include the camera head.

Advantageous Effects of Invention

The photoelectric composite module according to the present disclosure includes at least two printed boards: the first printed board configured to act as a relay between the contacts of the first connecting member and the photoelectric conversion element; and the second printed board configured to act as a relay between the contacts of the first connecting member and the electrical signal cable. Accordingly, when the photoelectric composite module according to the present disclosure is used in a camera head, the function of relaying, to the photoelectric conversion element, imaging signals (electrical signals) output by the image sensor is provided to a printed board (first printed board) while the function of relaying, to the image sensor, control signals and the like (electrical signals) output by the controller is provided to another separate printed board (second printed board). Thus, each of the first and second printed boards can be reduced in size as compared to a single printed board provided with these two functions.

In addition, the first and second printed boards reduced in size as described above are three-dimensionally arranged, in other words, are not arranged in the same plain face. Thus, as compared to employing a single printed board provided with the aforementioned two functions, the entire photoelectric composite module can be downsized.

The camera head according to the present disclosure includes the photoelectric composite module, thus exhibiting advantageous effects similar to those of the photoelectric composite module.

The endoscopic device according to the present disclosure includes the camera head, thus exhibiting advantageous effects similar to those of the camera head.

DESCRIPTION OF EMBODIMENT(S)

Figure 1:
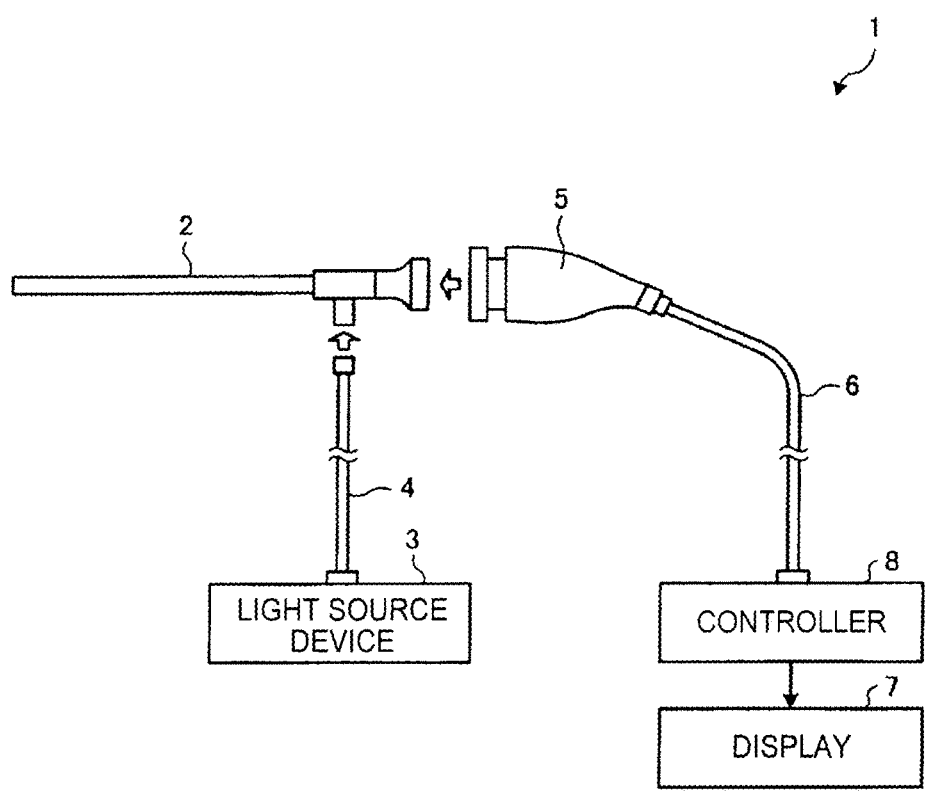
FIG. 1 shows a schematic configuration of an endoscopic device according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

[Schematic Configuration of Endoscopic Device]

FIG. 1 shows a schematic configuration of an endoscopic device 1 according to an embodiment of the present disclosure.

The endoscopic device 1 is an apparatus used in medical fields to observe the interior of an observation object (interior of a living body) such as a human being. Note that, though an endoscopic device using a rigid scope (insertion part 2) as shown in FIG. 1 will be described as the endoscopic device 1 in this embodiment, the endoscopic device 1 is not limited thereto, and may be an endoscopic device using a flexible scope (not shown).

As shown in FIG. 1, the endoscopic device 1 includes the insertion part 2, a light source device 3, a light guide 4, a camera head 5, a composite cable 6, a display 7, and a controller 8.

The insertion part 2, being rigid and having an elongated shape, is inserted into an observation object. An optical system for condensing light to form an object image is provided inside the insertion part 2.

The light source device 3 is connected to one end of the light guide 4, and supplies the one end of the light guide 4 with light to illuminate the interior of the observation object.

While the one end of the light guide 4 is detachably connected to the light source device 3, the other end is detachably connected to the insertion part 2. The light guide 4 transmits light supplied from the light source device 3 from the one end to the other end, thereby supplying the light to the insertion part 2. The light supplied to the insertion part 2 is emitted from the front end of the insertion part 2, and thereby the interior of the observation object is irradiated with the light. The light (object image) with which the interior of the observation object is irradiated is condensed by the optical system in the insertion part 2.

The camera head 5 is detachably connected to the base end of the insertion part 2. Under control of the controller 8, the camera head 5 images the object image formed with light condensed by the insertion part 2, then photoelectrically converts imaging signals (electrical signals) obtained by the imaging into optical signals, and outputs the optical signals.

The detailed configuration of the camera head 5 will be described later.

The composite cable 6 has a plurality of optical fibers 61 (see FIG. 6) and a plurality of electrical signal cables 62 (see FIG. 6) inside a jacket 6A (see FIG. 6), which is the outermost layer. One end of the composite cable 6 is detachably connected to the controller 8 while the other end is detachably connected to the camera head 5.

The plurality of optical fibers 61 are arranged at a center position of the composite cable 6 in a cross sectional view of the composite cable 6, and used for transmitting optical signals between the camera head 5 and the controller 8.

The plurality of electrical signal cables 62 are arranged around the plurality of optical fibers 61 in a cross sectional view of the composite cable 6, and used for transmitting electrical signals between the camera head 5 and the controller 8.

The display 7 displays an image under control of the controller 8.

The controller 8 acquires optical signals (imaging signals) output from the camera head 5 through the plurality of optical fibers 61, and photoelectrically converts the optical signals to electrical signals. Then, the controller 8 performs predetermined processing on the photoelectrically converted electrical signals, thereby causing the display 7 to display an image imaged by the camera head 5. Meanwhile, the controller 8 outputs control signals and the like (electrical signals) to the camera head 5 through the plurality of electrical signal cables 62.

[Configuration of Camera Head]

Figure 2:
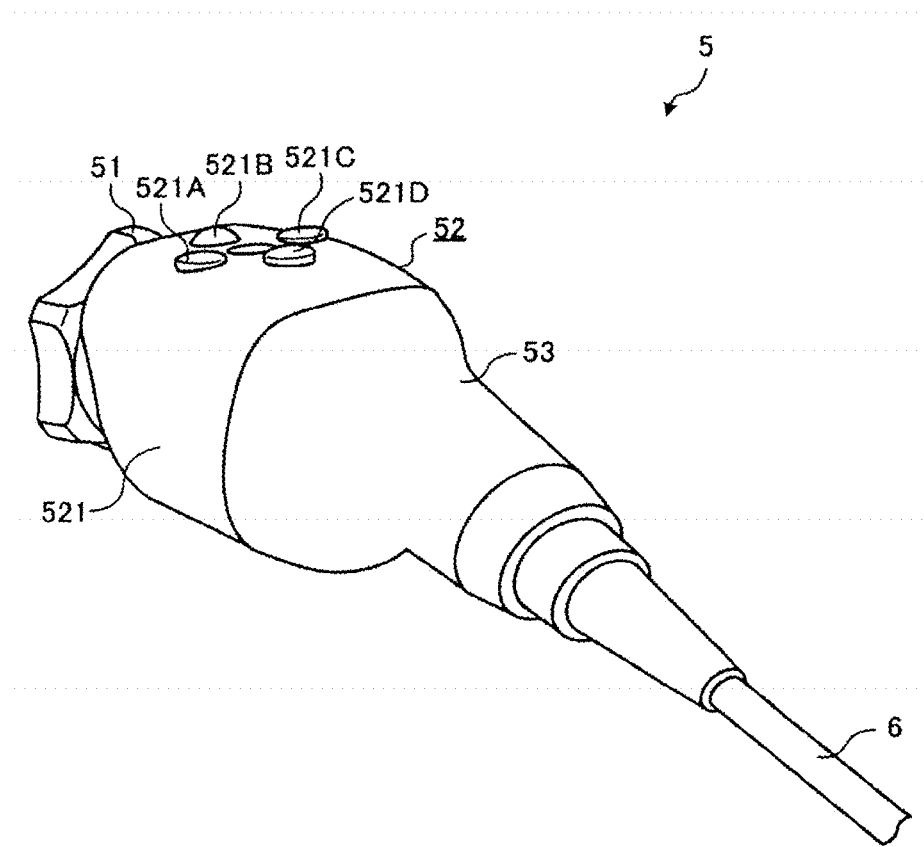
FIG. 2 is a perspective view, as viewed from a base-end side (side to which a composite cable is connected), of a camera head shown in FIG. 1.

FIG. 2 is a perspective view, as viewed from the base-end side (side to which the composite cable 6 is connected), of the camera head 5.

Figure 6:
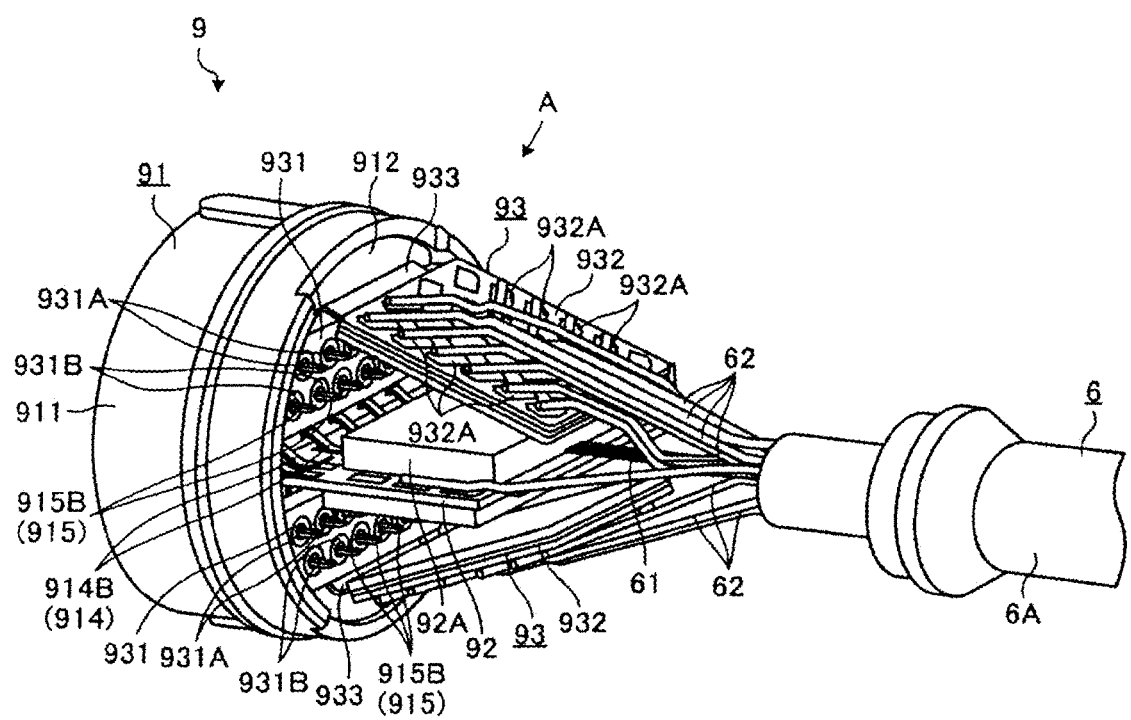
FIG. 6 is a perspective view, as viewed from the base-end side (side to which the composite cable is connected), of an internal structure of the photoelectric composite module shown in FIG. 5.

As shown in FIG. 2, the camera head 5 includes a coupler part 51, an airtight part 52, and a photoelectric composite module 9 (see FIG. 6).

Note that FIG. 2 shows the state in which a cover part 53, having a tubular shape to cover the photoelectric composite module 9 and the base-end side of the airtight part 52, is attached, thus not showing the photoelectric composite module 9.

The coupler part 51 is used for detachably connecting the camera head 5 to the base end of the insertion part 2, and provided at the front end of the camera head 5.

Figure 3:
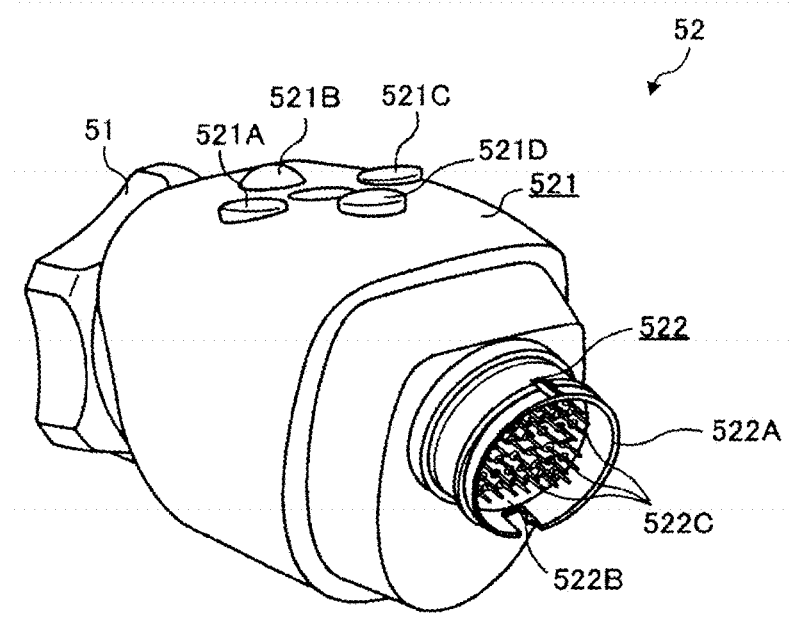
FIG. 3 is a perspective view, as viewed from the base-end side (side to which a photoelectric composite module is connected), of an airtight part shown in FIG. 2.

FIG. 3 is a perspective view, as viewed from the base-end side (side to which the photoelectric composite module 9 is connected), of the airtight part 52.

As shown in FIGS. 2 and 3, the airtight part 52 includes a casing 521 constituting the exterior of the airtight part 52, a hermetic connector 522 attached to the casing 521, and parts such as a lens unit (not shown), a driving motor (not shown), and an image sensor 523 (see FIG. 4) that are housed in the casing 521 in an airtight manner.

The lens unit forms an object image with light condensed by the insertion part 2 onto an imaging surface of the image sensor 523. The lens unit is movable in the optical axis direction.

The driving motor moves the lens unit along the optical axis when any of switches 521A to 521D (FIGS. 2 and 3), provided to be exposed on the outer surface of the casing 521, is pressed, thereby adjusting a focal distance and a focus of the lens unit.

The image sensor 523 includes a charge-coupled device (CCD) or a complementary metal-oxide-semiconductor (CMOS) that receives light condensed by the lens unit and converts the received light into electrical signals.

Figure 4:
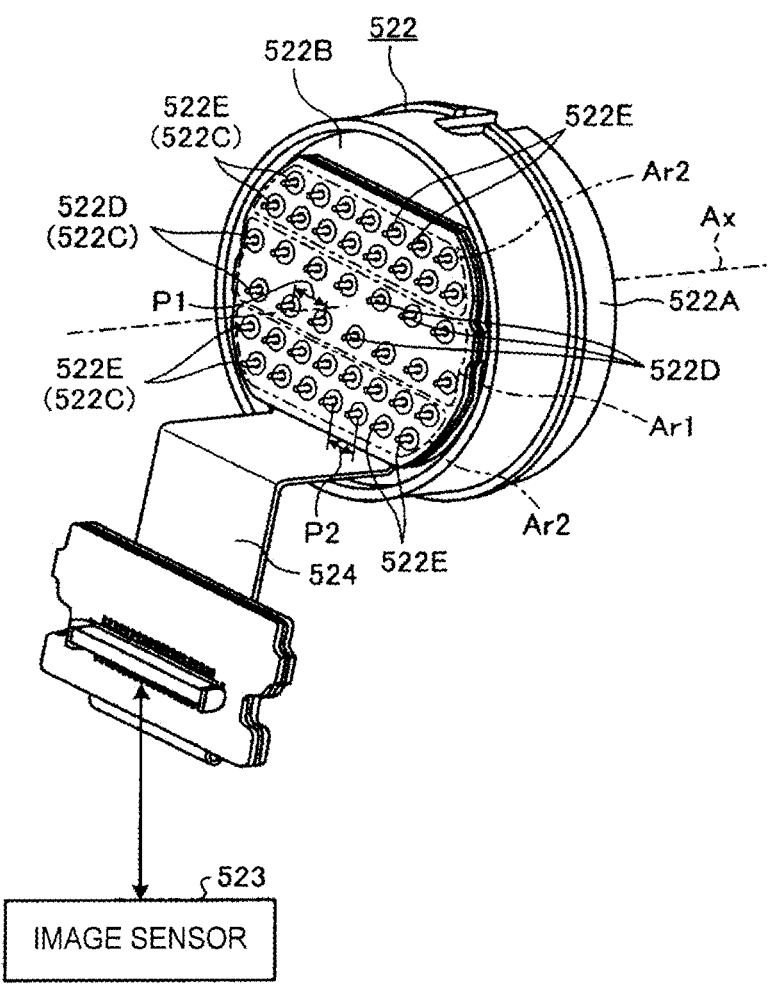
FIG. 4 is a perspective view, as viewed from an inside of the airtight part, of a hermetic connector shown in FIG. 3.

FIG. 4 is a perspective view, as viewed from the inside of the airtight part 52, of the hermetic connector 522.

The hermetic connector 522, being a member equivalent to a second connecting member according to the present disclosure, is attached to the base-end side (side to which the photoelectric composite module 9 is connected) of the casing 521 as shown in FIG. 3.

This hermetic connector 522 is a round connector and includes a second outer frame 522A, a plate body 522B and a plurality of conductive pins 522C as shown in FIGS. 3 and 4.

The second outer frame 522A is made of a metal material and has a cylindrical shape.

The plate body 522B is made of a metal material and has a disc shape. The plate body 522B closes the interior of the second outer frame 522A.

Each of the plurality of conductive pins 522C has a columnar shape. The plurality of conductive pins 522C are attached to the plate body 522B in the state of penetrating the plate body 522B from the front to the back and being insulated from one another.

Hereinafter, among the plurality of conductive pins 522C, the conductive pins 522C provided in a first area Ar1 indicated by the dashed-dotted line in FIG. 4 will be described as first conductive pins 522D. Meanwhile, among the plurality of conductive pins 522C, the conductive pins 522C provided in two second areas Ar2 indicated by the two-dot chain line will be described as second conductive pins 522E.

Here, when viewed from the direction along a central axis Ax of the second outer frame 522A (FIG. 4), the first area Ar1 is, in the second outer frame 522A, a band-shaped area including the central axis Ax and extending in a first direction (right-left direction in FIG. 4) orthogonal to the central axis Ax. Meanwhile, the two second areas Ar2 are areas other than the first area Ar1 in the second outer frame 522A, each being a band-shaped area extending in the first direction to be parallel to the first area Ar1.

In the first area Ar1, the plurality of first conductive pins 522D are arranged in two rows which are side by side in the up-down direction in FIG. 4.

More specifically, the plurality of first conductive pins 522D arranged side by side in the first row, which is the upper one, are arranged side by side at a first pitch P1 (FIG. 4). Similarly to the plurality of first conductive pins 522D arranged side by side in the first row, the plurality of first conductive pins 522D arranged side by side in the second row, which is the lower one, are also arranged side by side at the first pitch P1. In addition, each first conductive pin 522D in the second row is arranged at a center position, as viewed from above in FIG. 4, between adjacent first conductive pins 522D arranged side by side in the first row.

In each of the second areas Ar2, the plurality of second conductive pins 522E are arranged in two rows which are side by side in the up-down direction in FIG. 4.

More specifically, in the lower one of the second areas Ar2 in FIG. 4, the plurality of second conductive pins 522E arranged side by side in the first row, which is the upper one, are arranged side by side at a second pitch P2 (FIG. 4), which is smaller than the first pitch P1. Similarly to the plurality of second conductive pins 522E arranged side by side in the first row, the plurality of second conductive pins 522E arranged side by side in the second row, which is the lower one, are also arranged side by side at the second pitch P2. In addition, each second conductive pin 522E in the second row is arranged at a center position, as viewed from above in FIG. 4, between adjacent second conductive pins 522E arranged side by side in the first row.

The plurality of second conductive pins 522E arranged in the upper one of the second areas Ar2 in FIG. 4 are arranged symmetrically to the plurality of second conductive pins 522E arranged in the lower one of the second areas Ar2 with respect to a face passing through the central axis Ax and being parallel to the side-by-side arrangement direction of the second conductive pins 522E.

As shown in FIG. 4, an airtight-part side printed board 524, which acts as a relay between (electrically connects) the plurality of conductive pins 522C and the image sensor 523, is attached to the hermetic connector 522 on the inner side of the airtight part 52.

The airtight-part side printed board 524 relays, to the plurality of first conductive pins 522D, imaging signals (electrical signals) output by the image sensor 523. In addition, the airtight-part side printed board 524 relays, to the image sensor 523, control signals and the like (electrical signals) output by the controller 8 through the composite cable 6, the photoelectric composite module 9, and the plurality of second conductive pins 522E.

[Configuration of Photoelectric Composite Module]

Figure 5:
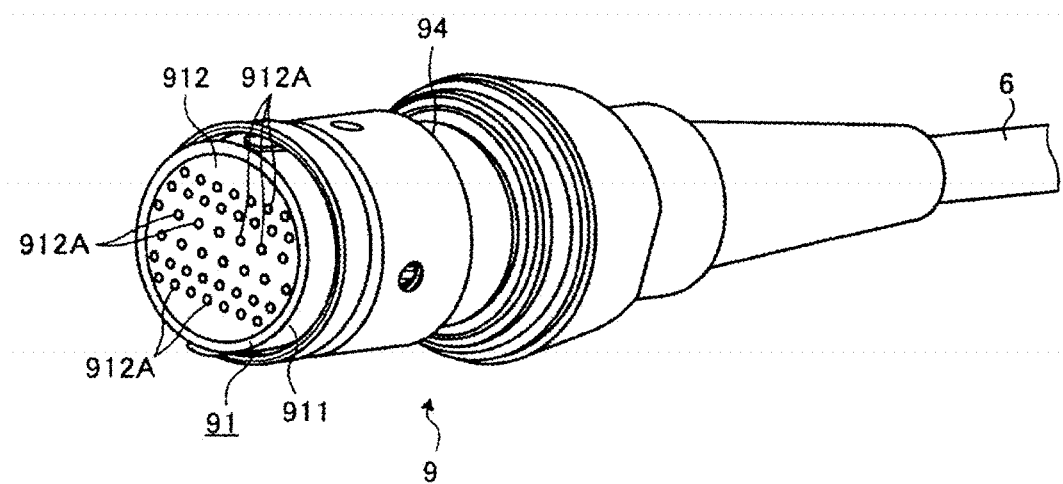
FIG. 5 is a perspective view, as viewed from a front-end side (side to which the airtight part is connected), of the photoelectric composite module according to an embodiment of the present disclosure.
Figure 7:
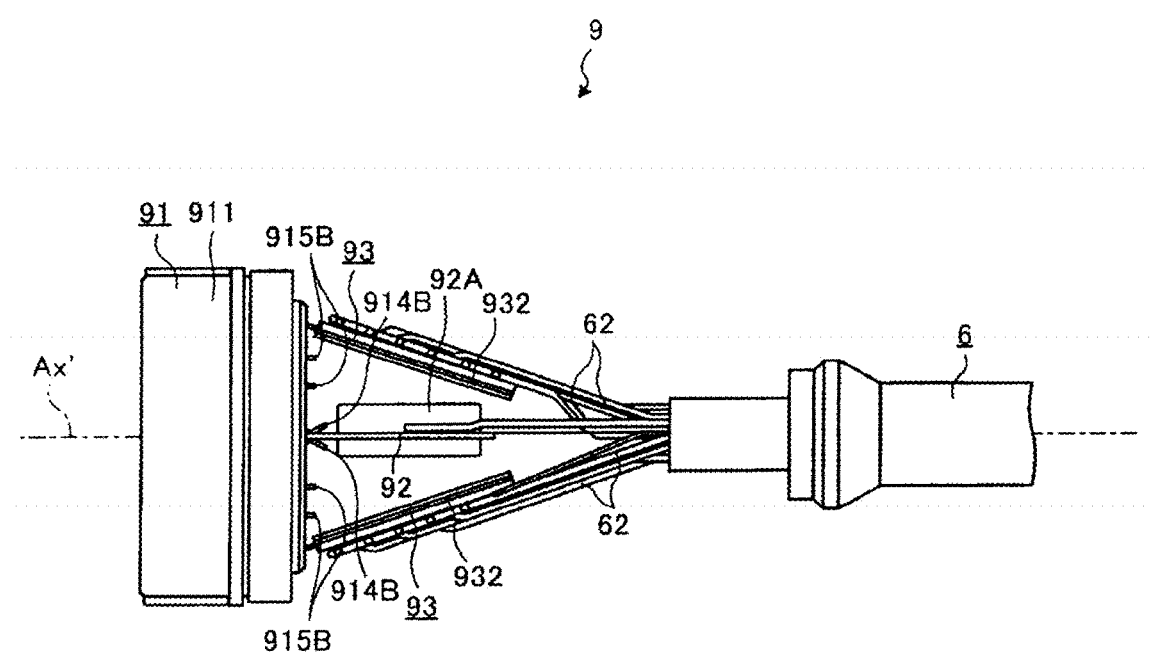
FIG. 7 is a side view of the internal structure of the photoelectric composite module shown in FIG. 5.

FIG. 5 is a perspective view, as viewed from the front-end side (side to which the airtight part 52 is connected), of the photoelectric composite module 9. FIG. 6 is a perspective view, as viewed from the base-end side (side to which the composite cable 6 is connected), of the internal structure of the photoelectric composite module 9. FIG. 7 is a side view of the internal structure of the photoelectric composite module 9.

The photoelectric composite module 9 is mechanically and electrically connected to the hermetic connector 522. The photoelectric composite module 9 converts imaging signals (electrical signals) output by the image sensor 523 into optical signals, and then outputs the optical signals to the composite cable 6 (the plurality of optical fibers 61). In addition, the photoelectric composite module 9 relays, to the hermetic connector 522 (image sensor 523), control signals and the like (electrical signals) output by the controller 8 through the plurality of electrical signal cables 62.

As shown in FIGS. 5 to 7, the photoelectric composite module 9 includes a receptacle 91, a first printed board 92 (FIGS. 6 and 7), two second printed boards 93 (FIGS. 6 and 7) and a covering member 94 (FIG. 5) which has a tubular shape and which covers the base-end side (side opposite to the side to which the hermetic connector 522 is connected) of the receptacle 91.

[Configuration of Receptacle]

Figure 8:
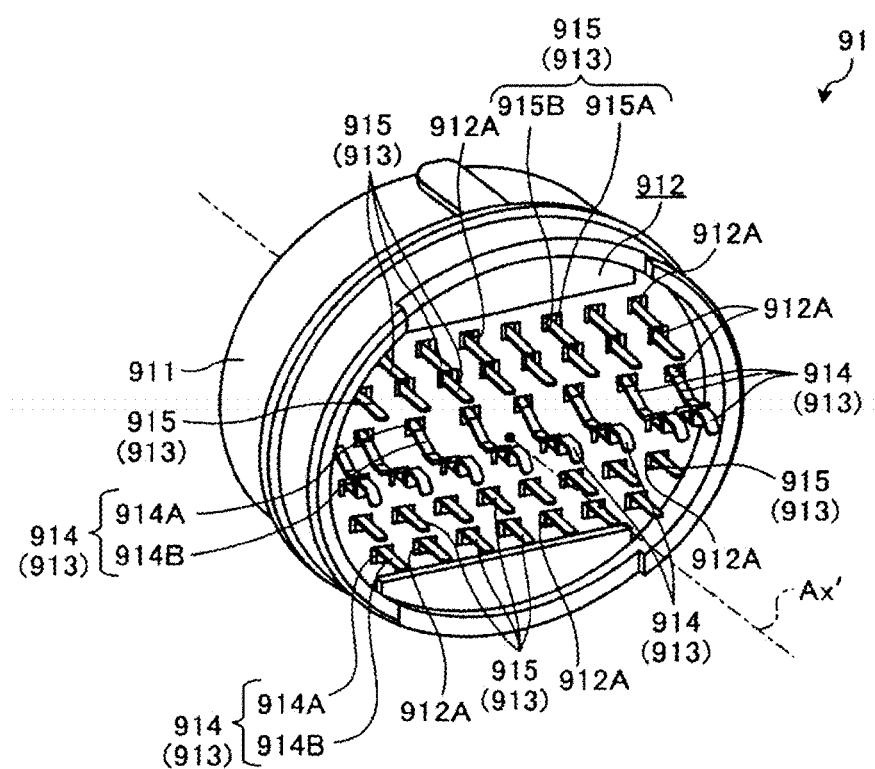
FIG. 8 is a perspective view, as viewed from the base-end side (side to which first and second printed boards are connected), of a receptacle shown in FIGS. 5 to 7.

FIG. 8 is a perspective view, as viewed from the base-end side, of the receptacle 91.

The receptacle 91, being a member equivalent to a first connecting member according to the present disclosure, is a round connector mechanically and electrically connected to the hermetic connector 522, and is provided at the front end of the photoelectric composite module 9.

As shown in FIG. 8, the receptacle 91 includes a first outer frame 911, an insulator 912, and a plurality of contacts 913.

The first outer frame 911 is made of a metal material and has a cylindrical shape.

The insulator 912 is made of an insulating material and closes the interior of the first outer frame 911.

As shown in FIGS. 5 and 8, in the insulator 912, there are formed a plurality of insertion holes 912A into which the plurality of conductive pins 522C of the hermetic connector 522 can be inserted when the hermetic connector 522 and the receptacle 91 are connected.

Each of the plurality of insertion holes 912A is formed in a stepped shape as viewed from the direction along a central axis Ax' of the first outer frame 911 (FIG. 8) in a manner that, in a cross sectional view, the insertion hole 912A has a round shape corresponding to the shape (columnar shape) of the conductive pin 522C at the front-end side (side to which the hermetic connector 522 is connected) of the receptacle 91, and a rectangular shape surrounding this front-end side portion at the base-end side of the receptacle 91.

As illustrated in FIG. 8, the plurality of contacts 913 are respectively provided inside the plurality of insertion holes 912A on the base-end side. Additionally, when the plurality of conductive pins 522C of the hermetic connector 522 are respectively inserted into the plurality of insertion holes 912A, the plurality of contacts 913 are electrically connected to the corresponding plurality of conductive pins 522C.

Figure 9:
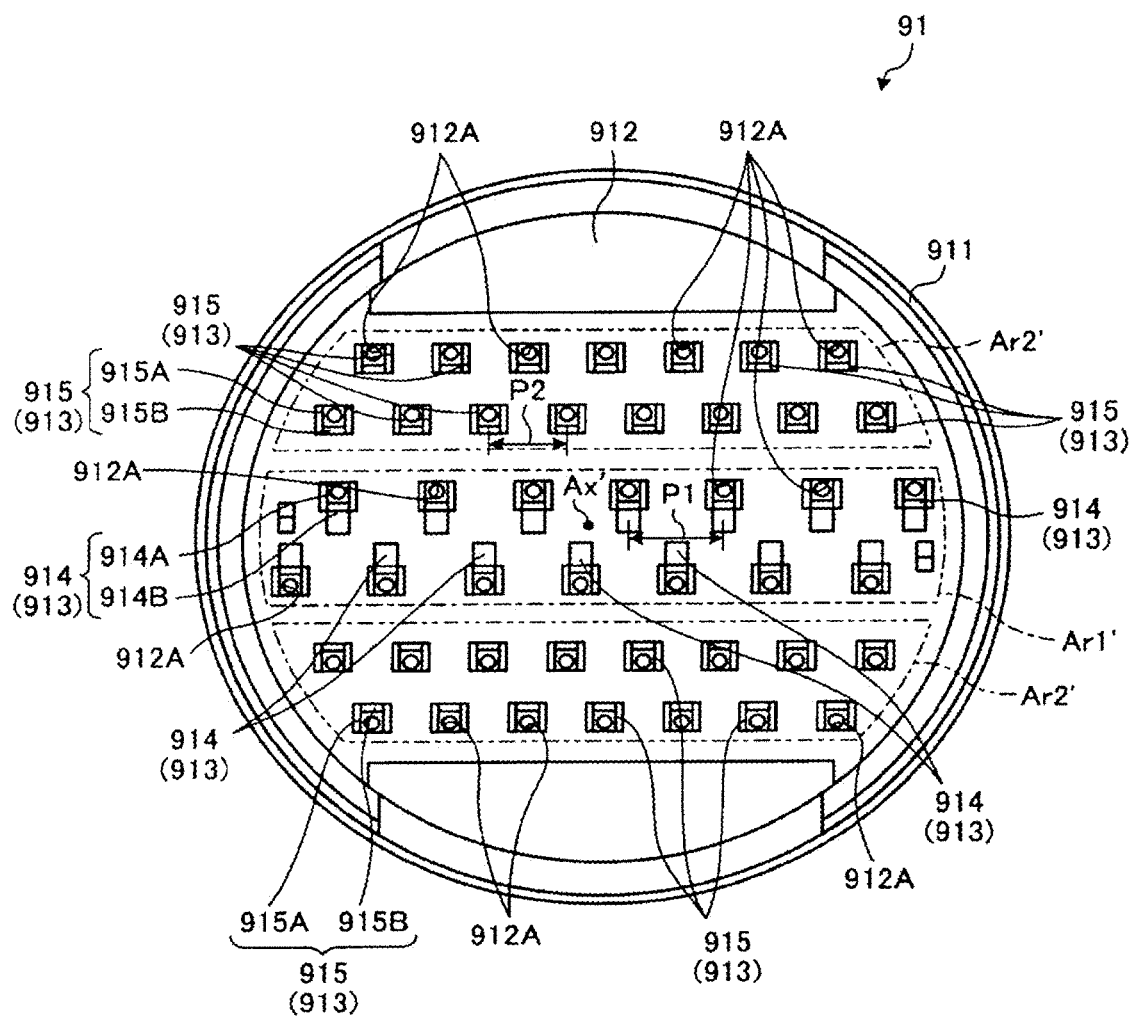
FIG. 9 shows an array state of a plurality of contacts shown in FIG. 8.

FIG. 9 shows an array state of the plurality of contacts 913.

Hereinafter, among the plurality of contacts 913, the contacts 913 provided in a first area Ar1' indicated by the dashed-dotted line in FIG. 9 will be described as first contacts 914. Meanwhile, among the plurality of contacts 913, the contacts 913 provided in two second areas Ar2' indicated by the two-dot chain line in FIG. 9 will be described as second contacts 915.

Here, when viewed from the direction along the central axis Ax' (FIG. 9) of the first outer frame 911, the first area Ar1', facing the first area Ar1 shown in FIG. 4, is, in the first outer frame 911, a band-shaped area including the central axis Ax' and extending in a first direction (right-left direction in FIG. 9) orthogonal to the central axis Ax'. In other words, the first area Ar1' is a radially extending band-shaped area including the central axis Ax' when viewed from the direction along the central axis Ax'. Meanwhile, the two second areas Ar2', facing the second areas Ar2 shown in FIG. 4, are areas other than the first area Ar1' in the first outer frame 911, each being a band-shaped area extending in the first direction to be parallel to the first area Ar1'.

The plurality of first contacts 914 are arranged similarly to the plurality of first conductive pins 522D. In other words, in the first area Ar1', the plurality of first contacts 914 are arranged in two rows which are side by side in the up-down direction in FIG. 9. In addition, the plurality of first contacts 914 are arranged side by side at the first pitch P1.

The plurality of second contacts 915 are arranged similarly to the plurality of second conductive pins 522E. In other words, in each of the second areas Ar2', the plurality of second contacts 915 are arranged in two rows which are side by side in the up-down direction in FIG. 9. In addition, the plurality of second contacts 915 are arranged side by side at the second pitch P2.

The plurality of first contacts 914 arranged as above have the same shape. Hereinafter, the shape of one of the first contacts 914 will be described.

As shown in FIGS. 8 and 9, the first contact 914 includes a first main contact body 914A and a first pin-shaped portion 914B.

The first main contact body 914A, provided to the inside of the insertion hole 912A, is formed in a substantially U shape when viewed from the direction along the central axis Ax' so as to extend along the central axis Ax'. When the conductive pins 522C are inserted into the insertion holes 912A, the inner periphery of the U shape of each first main contact body 914A abuts the outer periphery of the corresponding conductive pin 522C, so that the first main contact body 914A is electrically connected to the conductive pin 522C.

The first pin-shaped portion 914B protrudes while curving from a base-end portion of the U shape of the first main contact body 914A toward the base-end side (side where the first and second printed boards 92 and 93 are arranged) of the receptacle 91, and is formed in an elastically deformable leaf spring shape.

In addition, in FIG. 9, in the first area Ar1', the plurality of first contacts 914 arranged side by side in the first row, which is the upper one, are provided to the respective insertion holes 912A so that the opening of the U shape of the first main contact body 914A faces upward. Meanwhile, the plurality of first contacts 914 arranged side by side in the second row, which is the lower one, are provided to the respective insertion holes 912A so that the opening of the U shape of the first main contact body 914A faces downward.

The plurality of second contacts 915 arranged as above have the same shape. Hereinafter, the shape of one of the second contacts 915 will be described.

As shown in FIGS. 8 and 9, the second contact 915 includes a second main contact body 915A and a second pin-shaped portion 915B.

The second main contact body 915A is a part having a shape and a function similar to those of the first main contact body 914A.

The second pin-shaped portion 915B protrudes linearly along the central axis Ax' from a base-end portion of the U shape of the second main contact body 915A toward the base-end side of the receptacle 91.

In addition, in FIG. 9, the plurality of second contacts 915 arranged in the upper one of the second areas Ar2' are provided to the respective insertion holes 912A so that the opening of the U shape of the second main contact body 915A faces upward. Meanwhile, the plurality of second contacts 915 arranged in the lower one of the second areas Ar2' are provided to the respective insertion holes 912A so that the opening of the U shape of the second main contact body 915A faces downward.

[Configuration of First Printed Board]

The first printed board 92 is formed of a rigid substrate on which a photoelectric conversion element 92A for converting electrical signals into optical signals is mounted. The first printed board 92 is electrically connected to the plurality of first contacts 914 of the receptacle 91, and relays, to the photoelectric conversion element 92A, imaging signals (electrical signals) output by the image sensor 523 through the airtight-part side printed board 524, the plurality of first conductive pins 5221D, and the plurality of first contacts 914.

Here, as shown in FIG. 6, the plurality of optical fibers 61 are connected to the photoelectric conversion element 92A. In other words, the photoelectric conversion element 92A converts imaging signals (electrical signals) into optical signals, and then outputs the optical signals to the plurality of optical fibers 61.

As shown in FIG. 7, the first printed board 92 is arranged along the central axis Ax' on the base-end side of the receptacle 91.

Figure 10A:
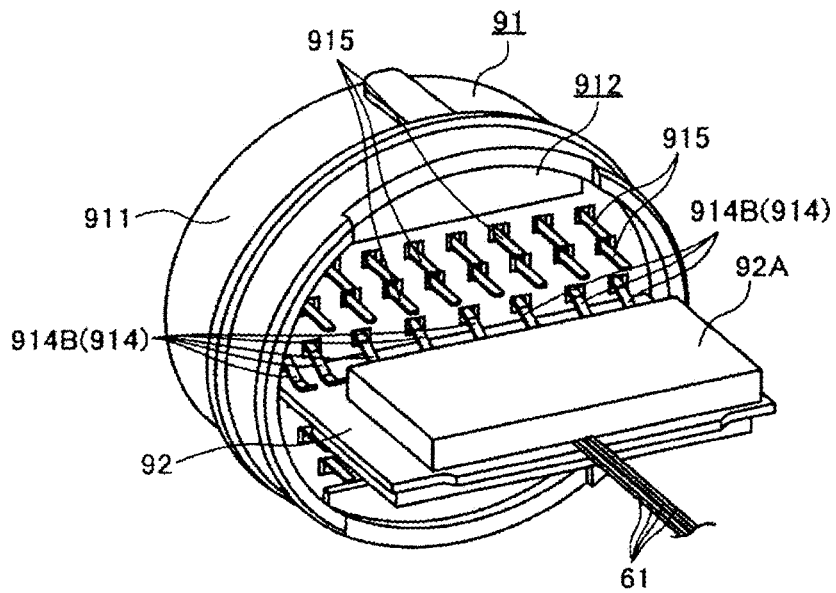
FIG. 10A is a perspective view, as viewed from the base-end side of the receptacle shown in FIGS. 6 and 7, of a state in which the first printed board is attached to the receptacle.
Figure 10B:
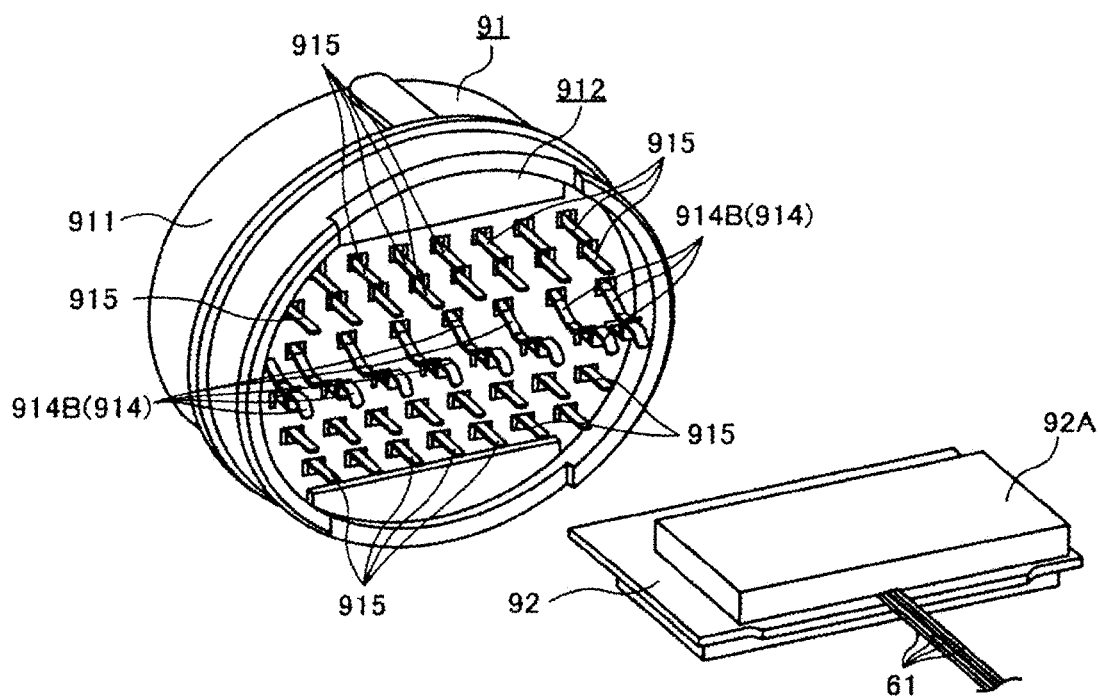
FIG. 10B is an exploded perspective view, as viewed from the base-end side of the receptacle shown in FIGS. 6 and 7, of a state in which the first printed board is detached from the receptacle.

FIG. 10A is a perspective view, as viewed from the base-end side of the receptacle 91, of a state in which the first printed board 92 is attached to the receptacle 91. FIG. 10B is an exploded perspective view showing a state in which the first printed board 92 is detached from the receptacle 91 shown in FIG. 10A.

Specifically, the first printed board 92 is attached to the receptacle 91 as described below.

In other words, the first printed board 92 is inserted between the first row, which is the upper one, of the plurality of first contacts 914 (first pin-shaped portions 914B) and the second row, which is the lower one, of the plurality of first contacts 914 (first pin-shaped portions 914B), in FIGS. 10A and 1013. In this state, the plurality of first pin-shaped portions 914B in the first and second rows hold the first printed board 92 therebetween while being elastically deformed by the pressing of the first printed board 92. In addition, the plurality of first pin-shaped portions 914B in the first and second rows are electrically connected to lands (not shown) formed on the front and back surfaces of the first printed board 92. The first pin-shaped portions 914B are respectively soldered to the lands in the above state, and thereby the first printed board 92 is attached to the receptacle 91.

[Configuration of Second Printed Board]

The two second printed boards 93 are each formed of a flexible substrate, at least part of which is bendable, and relay, to the plurality of second contacts 915, control signals and the like (electrical signals) output by the controller 8 through the plurality of electrical signal cables 62. In other words, the control signals and the like (electrical signals) relayed to the plurality of second contacts 915 are output to the image sensor 523 through the plurality of second conductive pins 522E and the airtight-part side printed board 524.

These two second printed boards 93 have the same configuration. Hereinafter, one of the second printed boards 93 will be described.

As shown in FIGS. 6 and 7, the second printed board 93 includes a first connecting part 931 (FIG. 6), a second connecting part 932, and an installation part 933 (FIG. 6), installed between the first and second connecting parts 931 and 932.

The first connecting part 931 has a shape corresponding to one of the second areas Ar2'. Additionally, in the first connecting part 931, there are formed a plurality of holes 931A (refer to FIGS. 6 and 11) respectively corresponding to the plurality of second contacts 915 (second pin-shaped portions 915B) arranged in the second area Ar2'.

As shown in FIG. 6, the first connecting part 931 is attached to the receptacle 91, by placing the first connecting part 931 on the base-end side end surface of the insulator 912 with the second contacts 915 inserted through the respective holes 931A, and then by soldering the second pin-shaped portions 915B to lands 931B (refer to FIGS. 6 and 11) provided on the peripheries of the holes 931A, respectively.

The second connecting part 932 is arranged at a position overlapping with the first printed board 92 in FIGS. 6 and 7 by bending the installation part 933 with respect to the first connecting part 931 attached to the receptacle 91, as shown in FIGS. 6 and 7. In other words, the installation part 933, being part of the second printed board 93, has a curved shape.

As described above, the first connecting part 931 is arranged so as to be substantially orthogonal to the first printed board 92. In other words, the first connecting part 931 is arranged in a plain face (vertical face orthogonal to the central axis Ax' in FIGS. 6 and 7) different from a plain face (horizontal face including the central axis Ax' in FIGS. 6 and 7) in which the first printed board 92 is arranged. Meanwhile, the second connecting part 932 is arranged so as to face the front or back surface of the first printed board 92. In other words, similarly to the first connecting part 931, the second connecting part 932 is also arranged in a plain face different from the plain face in which the first printed board 92 is arranged. The installation part 933 has a curved shape and is arranged in a face different from the plain face in which the first printed board 92 is arranged. Accordingly, the first and second printed boards 92 and 93 are three-dimensionally arranged, part of which (the first printed board 92 and the first connecting part 931 or the second connecting part 932) are in different plain faces, part of which (the first printed board 92 and the installation part 933) are in different faces, and part of which (the first printed board 92 and the second connecting part 932) overlap with each other.

Note that, though having been described as being in a plain face (having a planar shape) in the above embodiment, each of the first and second connecting parts 931 and 932 is not limited thereto. For example, at least either of the first and second connecting parts 931 and 932 may be formed in a curved shape similarly to the installation part 933.

As used herein, "plain face" means the plain face of the main part of a board (or component member) instead of an absolutely plain face.

Also, the state in which boards "overlap with each other" means a state in which the boards are lined up in a straight virtual line (vertical line orthogonal to the central axis Ax' in this embodiment) so that the front and back surfaces thereof intersect the virtual line. Accordingly, the state in which boards "overlap with each other" may include the state in which the boards are in contact with each other and the state in which the boards are spaced from each other.

As shown in FIG. 6, on a surface of each second connecting part 932, there are formed a plurality of lands 932A each having a substantially rectangular shape. The second connecting part 932 is electrically connected to the plurality of electrical signal cables by soldering the plurality of electrical signal cables 62 to the plurality of lands 932A.

Figure 11:
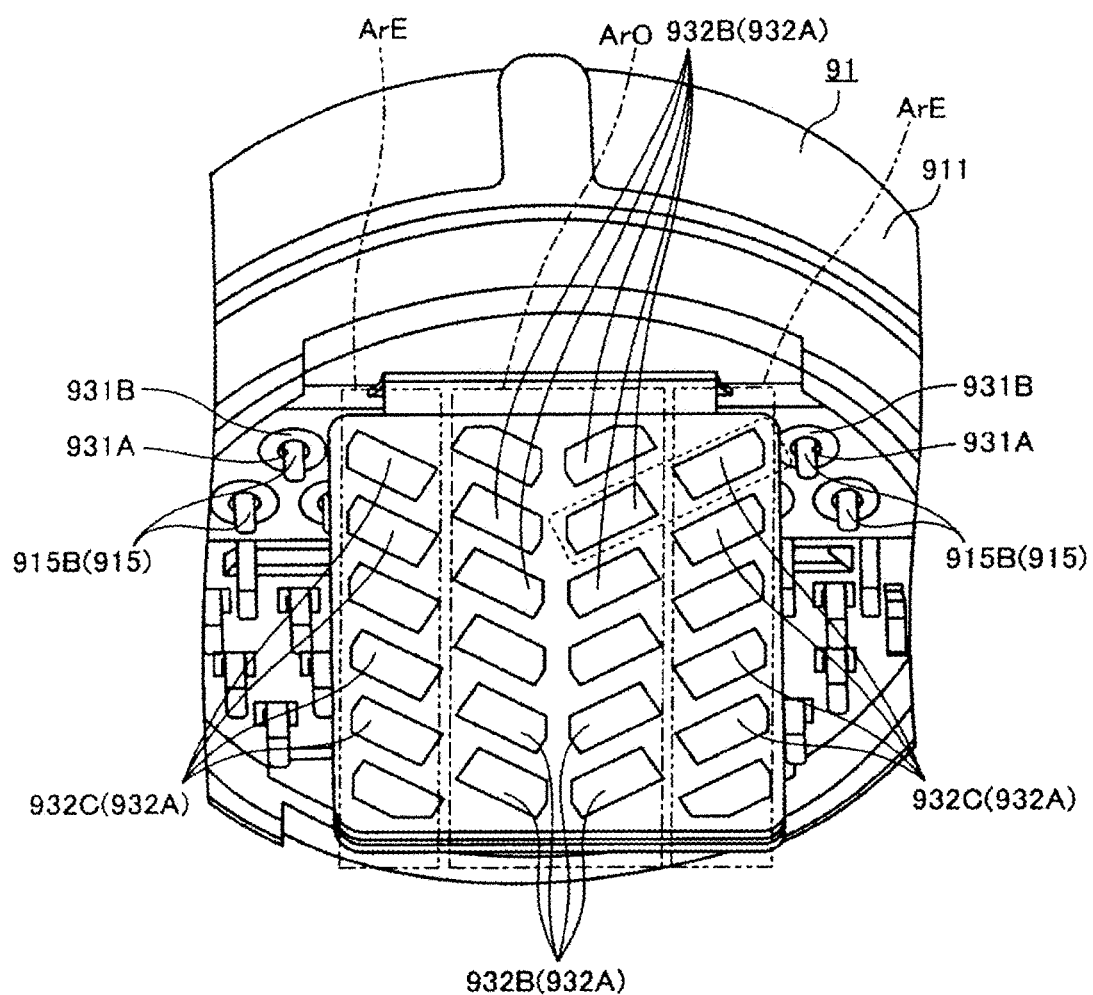
FIG. 11 shows an array state of a plurality of lands on a second connecting part shown in FIGS. 6 and 7.

FIG. 11 shows an array state of the plurality of lands 932A on the second connecting part 932. Specifically, FIG. 11 is a view, as viewed from above (from the direction A in FIG. 6), of the receptacle 91 to which only one of the second printed boards 93 (the second printed board 93 arranged at the upper position in FIG. 6) is attached.

Hereinafter, among the plurality of lands 932A, the lands 932A provided in a central area ArO indicated by the dashed-dotted line in FIG. 11 will be described as first lands 932B. Meanwhile, among the plurality of lands 932A, the lands 932A provided in two other areas ArE indicated by the two-dot chain line in FIG. 11 will be described as second lands 932C.

Here, the central area ArO is an area on the second connecting part 932 positioned at the center in the width direction thereof (right-left direction in FIG. 11 (equivalent to a second direction according to the present disclosure)). Meanwhile, the two other areas ArE are areas other than the central area ArO on the second connecting part 932.

In the central area ArO, the plurality of first lands 932B are arranged side by side in the up-down direction in FIG. 11 in two rows which are side by side in the width direction of the second connecting part 932.

More specifically, the plurality of first lands 932B arranged side by side in the first row, which is the left one with respect to the center of the second connecting part 932 in the width direction thereof in FIG. 11, are formed to be inclined downward in FIG. 11 toward the center of the width direction. Similarly, the plurality of first lands 932B arranged side by side in the second row, which is the right one with respect to the center in the width direction thereof in FIG. 11, are formed to be inclined downward in FIG. 11 toward the center of the width direction. In other words, pairs of the first lands 932B lying side by side in the width direction are arranged symmetrically about the center line connecting the centers in the width direction so as to form a substantially V shape.

The plurality of first lands 9328 are electrically connected respectively to a plurality of ground wires (not shown) constituting a conductor pattern provided to the second printed board.

In each of the other areas ArE, the plurality of second lands 932C are arranged side by side in the up-down direction in FIG. 11 in a row.

More specifically, the plurality of second lands 932C arranged side by side in the left one of the other areas ArE in FIG. 11 are formed to be each lined up with an adjacent one of the plurality of first lands 932B arranged side by side in the first row, which is the left one in FIG. 11, in the inclined direction of these first lands 932B, and to be inclined similarly to these first lands 932B. Similarly, the plurality of second lands 932C arranged side by side in the right one of the other areas ArE in FIG. 11 are formed to be each lined up with an adjacent one of the plurality of first lands 932B arranged side by side in the second row, which is the right one in FIG. 11, in the inclined direction of these first lands 932B, and to be inclined similarly to these first lands 932B.

The plurality of second lands 932C are electrically connected respectively to a plurality of signal wires (not shown) constituting a conductor pattern provided to the second printed board 93.

To the plurality of lands 932A, the plurality of electrical signal cables 62 are electrically connected in such a manner that each electrical signal cable 62 is electrically connected to a corresponding pair (the pair enclosed by the broken line in FIG. 11, for example) of the two of the first land 932B and the second land 932C lined up in either of the inclined directions of the lands 932A.

Figure 12:
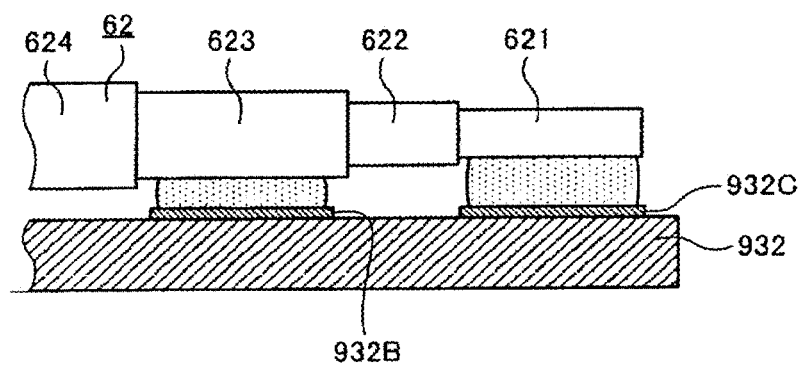
FIG. 12 shows a connected state between a pair of first and second lands shown in FIG. 11 and one electrical signal cable.

FIG. 12 shows a connected state between a pair of the first and second lands 932B and 932C and one of the electrical signal cables 62.

Here, each of the plurality of electrical signal cables 62 is formed of a coaxial cable.

Specifically, as shown in FIG. 12, each electrical signal cable 62 includes: a core wire 621; an insulation layer 622 covering the outer periphery of the core wire 621; a shield layer 623 covering the outer periphery of the insulation layer 622; and a covering layer 624 covering the outer periphery of the shield layer 623.

As shown in FIG. 12, each electrical signal cable 62 is arranged so that a front end portion thereof can be disposed on one of the aforementioned pairs of the first and second lands 932B and 932C so as to extend in the inclined direction thereof from the center of the second connecting part 932 in the width direction thereof. The electrical signal cable 62 disposed as above is electrically connected to the second connecting part 932 by soldering the core wire 621 and the shield layer 623 respectively to the second land 932C (signal wire) and the first land 932B (ground wire).

The photoelectric composite module 9 according to this embodiment includes three printed boards: the first printed board 92, which acts as a relay between the first contacts 914 of the receptacle 91 and the photoelectric conversion element 92A; and the two second printed boards 93, which acts as a relay between the second contacts 915 of the receptacle 91 and the electrical signal cables 62. Accordingly, the function of relaying, to the photoelectric conversion element 92A, imaging signals (electrical signals) output by the image sensor 523 is provided to a printed board (the first printed board 92) while the function of relaying, to the image sensor 523, control signals and the like (electrical signals) output by the controller 8 is provided to other separate printed boards (the second printed boards 93). Thus, each of the first and second printed boards 92 and 93 can be reduced in size as compared to a single printed board provided with these two functions.

In addition, the first and second printed boards 92 and 93 reduced in size as described above are three-dimensionally arranged, part of which (the first printed board 92 and the first or second connecting parts 931 or 932) are in different plain faces, part of which (the first printed board 92 and each of the installation parts 933) are in different faces, and part of which (the first printed board 92 and the second connecting parts 932) overlap with each other. Thus, as compared to employing a single printed board provided with the aforementioned two functions, the entire photoelectric composite module 9 can be downsized, and, consequently, the camera head 5 can be downsized.

Particularly, the first printed board 92 is formed of a rigid substrate having a planar shape and is arranged along the central axis Ax' on the base-end side of the receptacle 91, and the second printed boards 93 are each formed of a flexible substrate, at least part of which is bendable, and are arranged at positions facing the front and back surfaces of the first printed board 92. Thus, the first and second printed boards 92 and 93 can be easily set in the aforementioned three-dimensional arrangement. In addition, the first and second printed boards 92 and 93 can be compactly assembled, and thus the entire photoelectric composite module 9 can be further downsized.

In the photoelectric composite module 9 according to this embodiment, the plurality of first contacts 914 that relay imaging signals are provided in the first area Ar1' positioned at a center portion of the receptacle 91. Also, the first printed board 92 is arranged on the base-end side of the receptacle 91 in a center portion of the receptacle 91 when viewed from the direction along the central axis Ax'.

Thus, since the first printed board 92 is arranged in the center portion of the receptacle 91, a sufficiently wide pitch (first pitch P1) between the first contacts 914 can be secured to avoid inter-signal interference, even when differential signals are employed to transmit imaging signals output from the image sensor 523 to the controller 8 at high speed.

In the photoelectric composite module 9 according to this embodiment, the first printed board 92 is arranged along the central axis Ax' on the base-end side of the receptacle 91.

Accordingly, the optical fibers 61 can be connected to the photoelectric conversion element 92A mounted on the first printed board 92 without bending the optical fibers 61 arranged at the center of the composite cable 6.

In the photoelectric composite module 9 according to this embodiment, on a surface of each second printed board 93, the plurality of first lands 932B electrically connected to the ground wires are formed in the central area ArO, and the plurality of second lands 932C electrically connected to the signal wires are formed in the other areas ArE. In addition, the plurality of lands 932A are arranged symmetrically about the center line connecting the centers in the width direction of the second printed board 93 so as to form substantially V shapes.

Accordingly, when the plurality of electrical signal cables 62 are attached to the second printed board 93, the electrical signal cables 62 disposed along the surface of the second printed board 93 can be easily soldered thereto, which can simplify the fitting work.

In the photoelectric composite module 9 according to this embodiment, each of the plurality of first contacts 914 arranged side by side in upper and lower (FIG. 10) two rows includes the first pin-shaped portion 914B, which is elastically deformable.

Accordingly, by simply inserting the first printed board 92 between the first row of the plurality of first contacts 914 and the second row of the first contacts 914, the first printed board 92 can be attached to the receptacle 91 and electrically connected to the first contacts 914, which can simplify the fitting work.

In the photoelectric composite module 9 according to this embodiment, each of the second printed boards 93 is formed of a flexible substrate. In addition, the first connecting part 931 constituting the second printed board 93 has the holes 931A through which the second pin-shaped portions 915B of the second contacts 915 are inserted.

Accordingly, when the second printed board 93 are attached to the receptacle 91, soldering can easily be performed with the second pin-shaped portions 915B of the second contacts 915 inserted through the respective holes 931A and with the first connecting part 931 placed on the base-end side end surface of the insulator 912. This can simplify the fitting work. In addition, since the second printed board 93 is formed of a flexible substrate, by simply bending the second printed board 93 after the first connecting part 931 is attached to the receptacle 91 in the aforementioned manner, part (the second connecting part 932) of the second printed board 93 can be arranged at a position overlapping with the first printed board 92.

Other Embodiments

Hereinabove, an embodiment for carrying out the present disclosure has been described, but the present disclosure should not be limited only to the above embodiment.

Though two second printed boards 93 are provided to the photoelectric composite module 9 in the embodiment, the number of the second printed boards 93 is not limited thereto.

Figure 13:
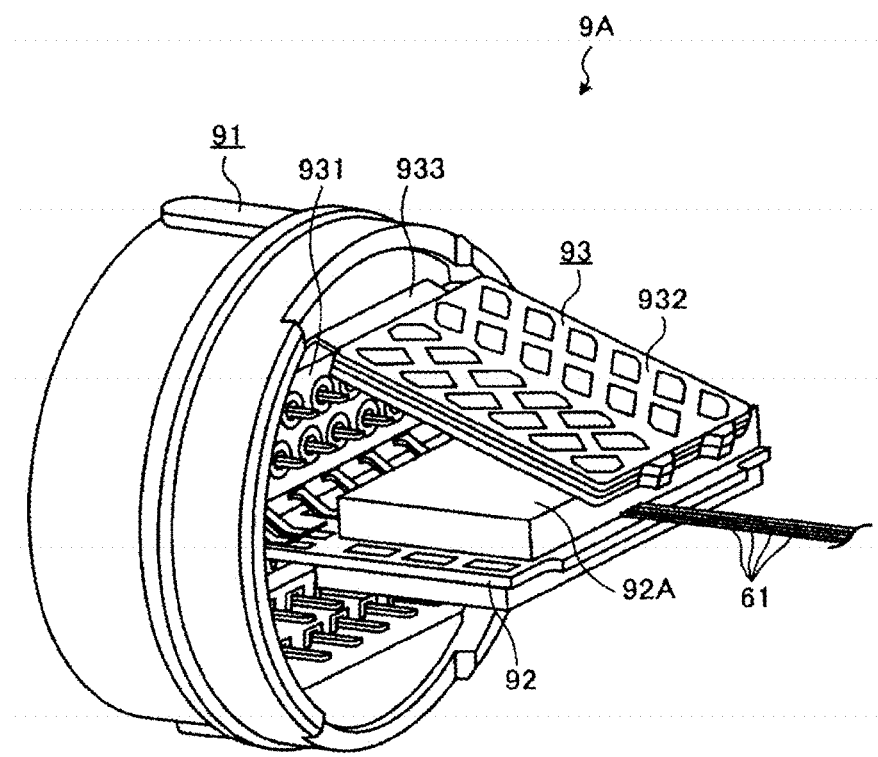
FIG. 13 shows a modification of an embodiment according to the present disclosure.

FIG. 13 shows a modification of the embodiment according to the present disclosure.

For example, like the a photoelectric composite module 9A shown in FIG. 13, a configuration provided with just one second printed board 93 may be employed. Also, though not shown, a configuration provided with three or more second printed boards 93 may be employed instead.

In the embodiment, the receptacle 91 is employed as the first connecting member according to the present disclosure, but the first connecting member is not limited thereto. The hermetic connector 522 may be used as the first connecting member according to the present disclosure. In other words, a configuration may be employed where the receptacle 91 is omitted, and the first and second printed boards 92 and 93 are connected from outside of the airtight part 52 to the hermetic connector 522 attached to the base-end side of the airtight part 52. In this case, each of the plurality of conductive pins 522C of the hermetic connector 522 is preferably formed in a shape similar to the first pin-shaped portions 914B of the receptacle 91 (in an elastically deformable leaf spring shape) in consideration of fitting work of the first printed board 92.

In the embodiment, round connectors (the receptacle 91 and the hermetic connector 522) are employed as the first and second connecting members according to the present disclosure, but connectors each having a non-round shape may be employed. When connectors each having a non-round shape are employed, a first printed board may be arranged at a position other than a center position of each connector (center position when viewed from the direction along the central axis of the connector) as long as a sufficiently wide pitch of a plurality of contacts electrically connected to the first printed board can be secured.

In the embodiment, the pitch (second pitch P2) of the plurality of second contacts 915 is set smaller than the pitch (first pitch P1) of the plurality of first contacts 914, but the pitch length is not limited thereto. The pitch of the plurality of second contacts 915 may be configured to be equal to or greater than that of the plurality of first contacts 914.

In the embodiment, as long as the first and second printed boards 92 and 93 are three-dimensionally arranged, or in other words are not arranged in the same plain face, the arrangement of the first and second printed boards 92 and 93 is not limited to that described above, and may be a different arrangement. Also, each of the first and second areas Ar1, Ar1', Ar2 and Ar2' may be a non-band-shaped area as long as the areas are independent of one another.

The endoscopic device 1 according to the embodiment may be used not only in medical fields but also in industrial fields, specifically, used as an endoscopic device for observing the interior of an observation object such as a machine structure.

Additionally, the present technology may also be configured as below.

(1)
A photoelectric composite module including:
 a first connecting member having
  an outer frame having a tubular shape, and
  a plurality of contacts provided in an interior of the outer frame:
 a first printed board on which a photoelectric conversion element configured to convert an electrical signal into an optical signal is mounted, and which is configured to act as a relay between the contacts and the photoelectric conversion element; and
 a second printed board configured to act as a relay between the contacts and an electrical signal cable,
 wherein the first printed board and the second printed board are three-dimensionally arranged.

(2)
The photoelectric composite module according to (1),
 wherein at least part of the first printed board and at least part of the second printed board are arranged in different plain faces.

(3)
The photoelectric composite module according to (1) or (2),
wherein at least part of the second printed board has a curved shape, and
wherein at least part of the first printed board and at least part of the second printed board are arranged in different faces.

(4)
The photoelectric composite module according to (3).
wherein the second printed board is formed of a flexible substrate, at least part of which is bendable.

(5)
The photoelectric composite module according to (3) or (4),
wherein the first printed board is formed of a rigid substrate having a planar shape.

(6)
The photoelectric composite module according to any one of (1) to (5),
wherein at least part of the first printed board and at least part of the second printed board are arranged in an overlapping manner.

(7)
The photoelectric composite module according to any one of (1) to (6),
wherein, when the interior of the outer frame is divided into a first area and a second area other than the first area as viewed from a direction along a central axis of the outer frame, the plurality of contacts include
a plurality of first contacts provided in the first area, and
a plurality of second contacts provided in the second area,
wherein the first printed board is electrically connected to the plurality of first contacts, and
wherein the second printed board is electrically connected to the plurality of second contacts.

(8)
The photoelectric composite module according to (7),
wherein, in the interior of the outer frame, the first area and the second area are band-shaped areas being parallel to each other and each extending in a first direction orthogonal to the central axis.

(9)
The photoelectric composite module according to (7) or (8),
wherein the first area is an area including the central axis.

(10)
The photoelectric composite module according to (9),
wherein the first area is a band-shaped area extending in a first direction orthogonal to the central axis.

(11)
The photoelectric composite module according to any one of (7) to (10),
wherein, in the first area, the plurality of first contacts are arranged side by side at a first pitch, and
wherein, in the second area, the plurality of second contacts are arranged side by side at a second pitch, which is smaller than the first pitch.

(12)
The photoelectric composite module according to (11),
wherein the outer frame has a cylindrical shape, and
wherein the first area is a band-shaped area including the central axis and extending in a radial direction of the outer frame.

(13)
The photoelectric composite module according to any one of (1) to (12),
wherein the first printed board is arranged along a central axis of the outer frame.

(14)
The photoelectric composite module according to any one of (1) to (13),
wherein the second printed board includes
a plurality of first lands electrically connected to ground wires constituting a conductor pattern provided to the second printed board, and formed in one of a central area and an other area, which excludes the central area, on a surface of the second printed board in a second direction along the surface, and
a plurality of second lands electrically connected to signal wires constituting a conductor pattern provided to the second printed board, and formed in the other of the central area and the other area, which excludes the central area, on the surface of the second printed board.

(15)
The photoelectric composite module according to (14),
wherein the one is the central area on the surface of the second printed board.

(16)
The photoelectric composite module according to (15),
wherein a plurality of the electrical signal cables each formed of a coaxial cable are provided,
wherein each of the plurality of electrical signal cables is electrically connected to a corresponding pair of the first land and the second land which is adjacent to the first land, and
wherein the first land and the second land of each of the pairs are formed to be lined up in an inclined direction with respect to the second direction on the surface of the second printed board.

(17)
The photoelectric composite module according to any one of (1) to (16),
wherein the first printed board is electrically connected to a plurality of first contacts arranged side by side in two rows in the interior of the outer frame, the plurality of first contacts being included in the plurality of contacts,
wherein the plurality of first contacts include respective first pin-shaped portions being elastically deformable and protruding toward a side where the first printed board and the second printed board are arranged, and
wherein, when the first printed board is inserted between a first row of the two rows of the first contacts and a second row of the two rows of the first contacts, a plurality of the first pin-shaped portions hold the first printed board while being elastically deformed, and are electrically connected to the first printed board.

(18)
The photoelectric composite module according to any one of (1) to (17),
wherein at least one of the plurality of contacts includes
a pin-shaped portion protruding toward a side where the first printed board and the second printed board are arranged, and
wherein the second printed board is formed of a flexible substrate having
a first connecting part having a hole through which the pin-shaped portion is inserted, the first connecting part being electrically connected to the at least one of the plurality of contacts, and a second connecting part arranged at a position overlapping with the first printed board when bent with respect to the first connecting part, the second connecting part being electrically connected to the electrical signal cable.

(19)

A camera head used in an endoscopic device, the camera head including:
a photoelectric composite module including
a first connecting member having
an outer frame having a tubular shape, and
a plurality of contacts provided in an interior of the outer frame,
a first printed board on which a photoelectric conversion element configured to convert an electrical signal into an optical signal is mounted, and which is configured to act as a relay between the contacts and the photoelectric conversion element, and
a second printed board configured to act as a relay between the contacts and an electrical signal cable, and three-dimensionally arranged with respect to the first printed board; and
an image sensor electrically connected to the first printed board and the second printed board through the first connecting member.

(20)

The camera head according to (19), further including:
a second connecting member mechanically and electrically connected to the first connecting member; and
a casing to which the second connecting member is attached,
wherein the image sensor is housed in the casing and electrically connected to the first printed board and the second printed board through the first connecting member and the second connecting member.

(21)

An endoscopic device including:
a camera head including
a photoelectric composite module including
a first connecting member having
an outer frame having a tubular shape, and
a plurality of contacts provided in an interior of the outer frame,
a first printed board on which a photoelectric conversion element configured to convert an electrical signal into an optical signal is mounted, and which is configured to act as a relay between the contacts and the photoelectric conversion element, and
a second printed board configured to act as a relay between the contacts and an electrical signal cable, and three-dimensionally arranged with respect to the first printed board, and
an image sensor electrically connected to the first printed board and the second printed board through the first connecting member.

REFERENCE SIGNS LIST 1 endoscopic device
2 insertion part
3 light source device
4 light guide
5 camera head
6 composite cable
7 display
8 controller
9 photoelectric composite module
51 coupler part
52 airtight part
53 cover part
61 optical fiber
62 electrical signal cables
91 receptacle
92 first printed board
92A photoelectric conversion element
93 second printed board
94 covering member
521 casing
522 hermetic connector
522A second outer frame
522B plate body
522C conductive pin
522D first conductive pin
522E second conductive pin
523 image sensor
524 airtight-part side printed board
621 core wire
622 insulation layer
623 shield layer
624 covering layer
911 first outer frame
912 insulator
912A insertion hole
913 contact
914 first contact
914A first main contact body
914B first pin-shaped portion
915 second contact
915A second main contact body
915B second pin-shaped portion
931 first connecting part
931A hole
93B land
932 second connecting part
932A land
932B first land
932C second land
933 installation part
A direction
Ar1, Ar1' first area
Ar2, Ar2' second area
ArE other area
ArO central area
Ax, Ax' central axis
P1 first pitch
P2 second pitch

The invention claimed is:

1. A medical connector comprising:
a first connecting member having an outer frame and a plurality of signal transmission paths provided in an interior of the outer frame;
a first printed board coupled to a first part of the signal transmission paths and on which is mounted a photoelectric converter configured to convert an electrical signal into an optical signal, the electrical signal being output from an image sensor; and
a second printed board coupled to a second part of the signal transmission paths different from the first part of the signal transmission paths,
wherein the first printed board and the second printed board are three-dimensionally arranged,
wherein the optical signal output from the photoelectric converter is transmitted exclusively over the first part of the signal transmission paths, and wherein a control signal for controlling operation of the image sensor is transmitted exclusively over the second part of the signal transmission paths.

2. The medical connector according to claim 1, where the electrical signal is received by the second printed board from the second part of the signal transmission paths.

3. The medical connector according to claim 1, wherein the first printed board acts as a relay that electrically connects one or more first contacts and the photoelectric converter, and the second printed board acts as a relay that electrically connects one or more second contacts and the second part of the signal transmission paths,
wherein the one or more first contacts are different than the one or more second contacts.

4. The medical connector according to claim 3, wherein the one or more first contacts are configured to receive the electrical signal from a medical imaging device having the image sensor.

5. The medical connector according to claim 1, wherein the first printed board and the second printed board are arranged in different planes.

6. The medical connector according to claim 1, wherein the second printed board is angled with respect to the first printed board.

7. The medical connector according to claim 1, wherein at least part of the second printed board has a curved shape, and wherein at least part of the first printed board and at least part of the second circuit board are arranged in different planes.

8. The medical connector according to claim 1, wherein the second printed board is formed of a flexible substrate, at least part of which is bendable.

9. The medical connector according to claim 1, wherein the first printed circuit board is formed of a rigid substrate having a flat planar shape.

10. The medical connector according to claim 1, wherein at least part of the first printed board and at least part of the second printed board are arranged in an overlapping manner.

11. The medical connector according to claim 1, wherein the second printed board includes a plurality of first lands that electrically connects to the second part of the signal transmission paths and constitute a first conductor pattern provided to the second printed circuit board and formed in a first area at a central area on the surface of the second printed circuit board, and a plurality of second lands electrically connected to the second part of the signal transmission paths and constitute a second conductor pattern provided to the second printed circuit board, and formed in a second area at other than the central area on the surface of the second printed circuit board.

12. The medical connector according to claim 11, wherein the first area is the central area and the second area is on both sides of the first area on the surface of the second printed board.

13. The medical connector according to claim 12, wherein the second part of the signal transmission paths is electrically connected to a corresponding pair of the first land and the second land which is adjacent to the first land, and
wherein the first lands and the second lands of each of the pairs are formed to be lined up in an inclined direction on the surface of the second printed board.

14. An endoscope system including:
electrical imaging circuitry configured to generate an electrical image signal; and
a photoelectric composite module, separated from the electrical imaging circuitry by a wall, that includes:
a first connecting member having an outer frame and a plurality of signal transmission paths provided in an interior of the outer frame;
a first printed board coupled to a first part of the signal transmission paths and on which is mounted a photoelectric converter configured to convert the electrical image signal into an optical signal; and
a second printed board coupled to a second part of the signal transmission paths different from the first part of the signal transmission paths,
wherein the first printed board and the second printed board are three-dimensionally arranged,
wherein the optical signal output from the photoelectric converter is transmitted exclusively over the first part of the signal transmission paths, and
wherein a control signal for controlling operation of the electrical imaging circuitry is transmitted exclusively over the second part of the signal transmission paths.

15. The endoscope system according to claim 14, further comprising control circuitry configured to convert the optical signal into a second electrical signal.

16. The endoscope system according to claim 15, wherein the control circuitry is further configured to process the converted second electrical signal.

17. The endoscope system according to claim 14, further comprising control circuitry configured to send control signals through the second part of the signal transmission paths.

18. The endoscope system according to claim 15, wherein the photoelectric composite module and the control circuitry are connected by a composite cable comprising optical fibers and electrical signal cables.

19. The endoscope system according to claim 14, wherein the endoscope system is a flexible endoscope system.

* * * * *